United States Patent
Myers et al.

(10) Patent No.: US 11,497,694 B2
(45) Date of Patent: *Nov. 15, 2022

(54) ORAL CARE COMPOSITIONS

(71) Applicant: Colgate-Palmolive Company, New York, NY (US)

(72) Inventors: Carl Myers, Wayne, NJ (US); Guillaume Picquet, Long Valley, NJ (US); Ekta Makwana, Monroe, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/215,028

(22) Filed: Dec. 10, 2018

(65) Prior Publication Data

US 2019/0175464 A1   Jun. 13, 2019

Related U.S. Application Data

(60) Provisional application No. 62/597,970, filed on Dec. 13, 2017.

(51) Int. Cl.
| | | |
|---|---|---|
| *A61K 8/24* | (2006.01) | |
| *A61K 8/86* | (2006.01) | |
| *A61Q 11/00* | (2006.01) | |
| *A61K 8/49* | (2006.01) | |
| *A61K 8/81* | (2006.01) | |
| *A61K 8/44* | (2006.01) | |
| *A61K 8/90* | (2006.01) | |
| *A61K 8/41* | (2006.01) | |

(52) U.S. Cl.
CPC .................. *A61K 8/24* (2013.01); *A61K 8/41* (2013.01); *A61K 8/44* (2013.01); *A61K 8/4926* (2013.01); *A61K 8/8147* (2013.01); *A61K 8/86* (2013.01); *A61K 8/90* (2013.01); *A61Q 11/00* (2013.01); *A61K 2800/43* (2013.01); *A61K 2800/52* (2013.01); *A61K 2800/592* (2013.01); *A61K 2800/594* (2013.01)

(58) Field of Classification Search
CPC .............. A61Q 11/00; A61K 2800/592; A61K 2800/594; A61K 8/24; A61K 8/41; A61K 8/44; A61K 8/4926; A61K 8/8147; A61K 8/86; A61K 8/90; A61K 8/60; A61K 9/1635; A61K 31/4155; A61K 8/49; A61K 9/0014; A23L 27/74

See application file for complete search history.

(56) References Cited

U.S. PATENT DOCUMENTS

| | | | |
|---|---|---|---|
| 8,926,997 B1 | 1/2015 | Sawyer | |
| 9,408,794 B2 * | 8/2016 | Lewus | A61K 8/347 |
| 9,814,666 B2 | 11/2017 | Prencipe | |
| 2008/0248072 A1 | 10/2008 | Glandorf | |
| 2014/0377194 A1 * | 12/2014 | Strand | A61K 8/24 424/57 |
| 2016/0331670 A1 | 11/2016 | Prencipe et al. | |
| 2017/0151158 A1 * | 6/2017 | Myers | A61K 8/41 |

FOREIGN PATENT DOCUMENTS

| | | |
|---|---|---|
| CN | 105980012 | 9/2016 |
| WO | 2015/094331 | 6/2015 |
| WO | 2014/094225 | 6/2017 |
| WO | 2017/096000 | 6/2017 |
| WO | 2017/106763 | 6/2017 |
| WO | 2017/112667 | 6/2017 |
| WO | 2017/223493 | 12/2017 |
| WO | 2018/031357 | 2/2018 |

OTHER PUBLICATIONS

International Search Report and the Written Opinion of the International Searching Authority issued in International Application PCT/US2018/064730 (dated Jun. 20, 2019).

International Search Report of the International Searching Authority in International Application No. PCT/US2016/064349, dated Feb. 27, 2017.

* cited by examiner

*Primary Examiner* — Lezah Roberts

(57) ABSTRACT

This application provides, among other things, novel aqueous monophasic compositions useful for combining and delivering poorly compatible ingredients, for example to deliver effective levels of cationic antibacterial agents in combination with anionic polymers, e.g. that protect against erosion and staining, by addition of a stabilizing amount of a polyamine, e.g. lysine, and methods for making and using the same.

10 Claims, No Drawings

ORAL CARE COMPOSITIONS

CROSS-REFERENCE TO RELATED APPLICATIONS

This application claims priority to U.S. Provisional Application No. 62/597,970, filed on Dec. 13, 2017, the contents of which are hereby incorporated by reference in its entirety.

BACKGROUND

This application relates, inter alia, to novel aqueous compositions useful for combining and delivering poorly compatible ingredients, for example to deliver effective levels of cationic antibacterial agents in combination with polymers that protect against erosion and staining.

Biofilms form when bacteria adhere to surfaces in some form of watery environment and begin to excrete a slimy, glue-like substance that can stick to all kinds of materials—metals, plastics, soil particles, medical implant materials, biological tissues. Dental plaque is a biofilm that adheres to tooth and other oral surfaces, particularly at the gingival margin, and is implicated in the occurrence of gingivitis, periodontitis, caries and other forms of periodontal disease. Dental plaque is cohesive and highly resistant to removal from teeth and/or oral surfaces. Bacteria associated with dental plaque convert sugar to glucans, which are insoluble polysaccharides that provide plaque with its cohesive properties. Anaerobic bacteria in plaque metabolize sugar to produce acids that dissolve tooth minerals, damaging the enamel and eventually forming dental caries. Saliva can buffer acids produced by bacteria and promote remineralization of the enamel, but extensive plaque can block the saliva from contact with the enamel. Redeposition of minerals in the biofilm forms a hard deposit on the tooth called calculus (or tartar), which becomes a local irritant for the gums, causing gingivitis.

Various antibacterial agents can retard the growth of bacteria and thus reduce the formation of biofilm on oral surfaces. In many cases, these antibacterial agents are cationic, for example quaternary ammonium surfactants such as cetyl pyridinium chloride (CPC), bisguanides such as chlorhexidine, metal cations such as zinc or stannous ions, and guanidines such as arginine.

Everyday activities such as smoking or other oral use of tobacco products, and eating, chewing or drinking certain foods and beverages (particularly coffee, tea, cola drinks, and red wine), cause undesirable staining of surfaces of teeth. Staining can also result from microbial activity, including that associated with dental plaque. The chromogens or color causing substances in these materials become part of the pellicle layer and can permeate the enamel layer. Even with regular brushing and flossing, years of chromogen accumulation can impart noticeable tooth discoloration.

A tooth is comprised of an inner dentin layer and an outer hard enamel layer that is the protective layer of the tooth. The enamel layer of a tooth is naturally opaque, and white or a slightly off-white color. The enamel layer is composed of hydroxyapatite mineral crystals that create a somewhat porous surface. These hydroxyapatite crystals form microscopic hexagonal rods or prisms that make up the enamel surface. As a result, the surface of the enamel presents microscopic spaces or pores between the prisms. Without limiting the mechanism, function, or utility of the present disclosure, it is believed that this porous nature of the enamel is where discoloring substances permeate the enamel and discolor the teeth.

As the compounds that stain the teeth are typically anionic materials, cationic antibacterial agents can cause or enhance staining by facilitating the deposit of chromogens or by forming salts with minerals. As these positively charged antibacterial agents deposit on the tooth surface, they attract negatively charged staining molecules from highly colored food and drink (coffee, tea, wine, etc.).

Anionic polymers have been shown to reduce staining and erosion as well as reduce biofilm formation can help coat and protect the enamel, discouraging bacterial attachment and repelling chromagens. These polymers, however, can interact with cationic antimicrobial agents, leading to formulation incompatibilities, particularly in high water formulations, such as mouthwashes, and inhibiting delivery of the antimicrobial agent and/or the polymer. Oral care products comprising such polymers are disclosed, for example, in WO 2015094336 A1, incorporated herein by reference. Furthermore, the presence of polyphosphates in compositions is also known to unfavorably interact with cationic components. For example, such cationic antibacterial agents are known to complex with these polyphosphates, which results in an unfavorable loss in antibacterial efficacy.

One approach of communicating that a formulation maintains the efficacy of anionic polymers and cationic antimicrobial agents is through the use of a biphasic system that generally separates these components into two distinct liquid phases. However, due to necessary ratios of components in biphasic systems, such compositions have relatively high viscosities. This viscosity makes handling during production less efficient and increases the cost of large-scale production.

There is thus a need for novel compositions and methods that minimize interactions between incompatible ingredients in a monophasic formulation and inhibit staining and/or biofilm formation, while also maintaining optimal handling characteristics and having a formulation that facilitates cost-efficient production.

BRIEF SUMMARY

It is surprisingly found that formulations comprising an aqueous solution of an anti-attachment agent comprising one or both of an acidic polymer and at least one polyphosphate; a nonionic polymer, e.g. a poly(alkylene oxide); a cationic active agent; a polyamine compound, e.g., lysine in free or salt form; and water, can form a stable monophasic system, which maintains the anti-bacterial efficacy of the cationic agent while also mitigating the stain-inducing properties of said cationic agent. In various embodiments, the compositions of the present disclosure provide extended anti-bacterial effects, i.e., anti-bacterial effects lasting, for example, 18 hours after use.

For example, cetyl pyridinium chloride (CPC) is useful as an antibacterial agent, while anionic polymers may be useful to help remove and inhibit staining. These ingredients are generally incompatible because they interact, resulting in reduced efficacy both ingredients or even precipitation of both components. The addition of lysine provides needed stability and competition between the acid functional groups of the polymer, the acid and the amine functional groups of lysine, and the CPC—the result is to free CPC and make it more available for interaction with bacteria. In some embodiments, the addition of glutamic acid further improves CPC availability through additional competition pathways through the carboxylates on glutamic acid. Without lysine (and optionally glutamic acid), a formulation with CPC and anionic polymers may have little better efficacy than a non-CPC containing material, or the media control.

Similarly, chlorhexidine will generally complex with anionic polymers no matter what steps are taken, given their high charge density and entropically driven precipitation reaction. But we have found that chlorhexidine and anionic polymers can be formulated in such a way to prevent precipitation (or to re-dissolve the precipitate) through the inclusion of one or more polyphosphates, lysine (Lys), and polyethylene glycol (PEG). Additionally, a non-ionic surfactant, e.g., poloxamer, can be used to supplement the composition.

The disclosure thus provides, in one embodiment, compositions comprising an aqueous solution of
(i) an anti-attachment agent comprising one or more of an acidic polymer, e.g., a phosphate/acrylate co-polymer, for example a polymer made up of acrylate monomers and phosphate-bearing monomers, e.g., a co-polymerized product of a mixture of acrylic acid, methacrylic acid, and a mixture of compounds of Formula 1:

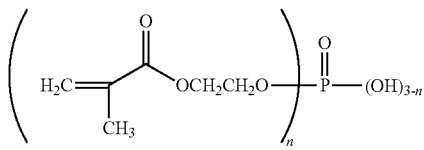

wherein n is 0, n is 1 and n is 2; and mixtures thereof; e.g., wherein the orally acceptable acidic polymer has a molecular weight of at least 7500 D, e.g., 10 kD to 1500 kD and at least one polyphosphate, wherein the polyphosphate comprises sodium tripolyphosphate, tetrasodium pyrophosphate, sodium acid pyrophosphate, tetrapotassium pyrophosphate, sodium hexametaphosphate or combinations thereof;
(ii) a nonionic polymer, for example selected from one or more poly(alkylene oxide) polymers, e.g., selected from polyethylene glycols, polypropylene glycols, poloxamers and mixtures thereof; e.g., wherein the nonionic polymer has a molecular weight of at least 3000 D, e.g., 6 kD to 250 kD, e.g., 8 kD;
(iii) a stabilizing amount of a polyamine, e.g., having an isoelectric point of greater than pH 8.5, e.g., lysine, e.g., which may be added in free or salt form;
(iv) a cationic active agent, e.g. one or more of quaternary ammonium surfactants (such as cetyl pyridinium chloride (CPC), benzalkonium chloride, cetyl trimethylammonium bromide or chloride, didecyldimethylammonium chloride, benzethonium chloride), bisguanides (such as chlorhexidine digluconate), cationic amino acids (such as arginine), metal cations (such as zinc, calcium, or stannous ions), or combinations thereof, and
(v) water.

The disclosure further provides methods of using such compositions, for example, inhibiting dental erosion, staining, and/or biofilm formation.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

As is usual in the art, the compositions described herein are sometimes described in terms of their ingredients, notwithstanding that the ingredients may disassociate, associate or react in the formulation. Ions, for example, are commonly provided to a formulation in the form of a salt, which may dissolve and disassociate in aqueous solution. It is understood that the invention encompasses both the mixture of described ingredients and the product thus obtained.

In a first embodiment, the disclosure provides a single phase composition (Composition
1) comprising an aqueous solution of
an anti-attachment agent;
a nonionic polymer having a molecular weight of about 5 kDa to 35 kDa;
a cationic active agent;
a stabilizing amount of a polyamine compound in free or salt form; and water,
wherein the anti-attachment agent comprises one or both of an acidic polymer and at least one polyphosphate.

For example, the disclosure provides embodiments of Composition 1 as follows:
1.1 Composition 1 or 1.1, wherein the polyphosphate comprises sodium tripolyphosphate, tetrasodium pyrophosphate, sodium acid pyrophosphate, tetrapotassium pyrophosphate, sodium hexametaphosphate or combinations thereof.
1.2 Any foregoing composition, wherein the polyphosphate comprises a combination of sodium tripolyphosphate and sodium acid pyrophosphate.
1.3 Any foregoing composition, wherein the polyphosphate consists of a combination of sodium tripolyphosphate and sodium acid pyrophosphate.
1.4 Any foregoing composition, wherein the at least one polyphosphate is present in an amount of about 0.1-5 weight % based on the total weight of the composition, 0.5-1.5 weight % based on the total weight of the composition, or 1 weight % based on the total weight of the composition.
1.5 Any foregoing composition, wherein the at least on polyphosphate comprises sodium tripolyphosphate in an amount of 0.1-2.5 weight % and sodium acid pyrophosphate in an amount of 0.1-2.5 weight % based on the total weight of the composition; or sodium tripolyphosphate in an amount of 0.3-1.2 weight % and sodium acid pyrophosphate in an amount of 0.3-1.2 weight % based on the total weight of the composition; or sodium tripolyphosphate in an amount of 1 weight % and sodium acid pyrophosphate in an amount of 1 weight % based on the total weight of the composition.
1.6 Any foregoing composition wherein the acid polymer is in linear or branched form or mixtures thereof, having acidic functional groups to provide an isoelectric point of pH 5 or less, and optionally additionally having uncharged spacers or side chains, for example comprising hydrophobic moieties (such as methyl methacrylate monomers or alkane chains), and/or uncharged hydrophilic moieties (such as polyalkylene glycols).

1.7 Any foregoing composition wherein the acidic polymer is selected from one or more of synthetic anionic linear or branched polycarboxylates, phosphate/acrylate co-polymers, linear or branched sulfates and combinations thereof.

1.8 Any foregoing composition wherein the acidic polymer is selected from one or more of co-polymerized products of a mixture of acrylic acid, methacrylic acid, and a mixture of compounds of Formula 1:

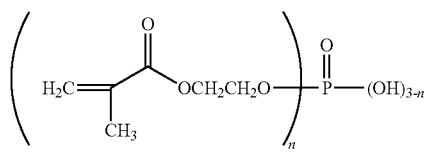

wherein n is 0, n is 1 and n is 2; and mixtures thereof; e.g., wherein the orally acceptable acidic polymer has a molecular weight of at least 7500 D, e.g., 10 kD to 1500 kD.

1.9 Any foregoing composition wherein the acidic polymer comprises a phosphate/acrylate co-polymer which is a co-polymerized product of a mixture of acrylic acid, methacrylic acid, and a mixture of compounds of Formula 1:

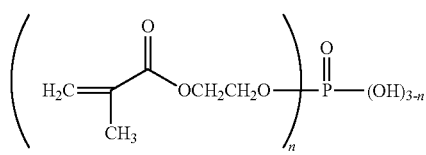

wherein n is 0, n is 1 and n is 2.

1.10 Any foregoing composition wherein the acidic polymer comprises a phosphate/acrylate co-polymer, wherein the phosphate/acrylate co-polymer is a co-polymerized product of a mixture of acrylic acid, methacrylic acid, and 2-hydroxyethyl methacrylate phosphates of Formula 1 comprising acrylic acid in a molar percentage of 80-90%, e.g., about 85%; methacrylic acid in a molar percentage of 5-15%, e.g., about 11%, and hydroxyethyl methacrylate phosphates of Formula 1 in a molar percentage of 2-6%, e.g., about 4%.

1.11 Any foregoing composition wherein the acidic polymer comprises a phosphate/acrylate co-polymer, wherein the phosphate/acrylate co-polymer has an average molecular weight of from 10 to 40 kDa, e.g., 20 to 30 kDa.

1.12 Any foregoing composition wherein the acidic polymer comprises a phosphate/acrylate co-polymer, wherein the phosphate/acrylate copolymer is a random copolymer having a weight average molecular weight of about 20,000 to 30,000 grams per mole that is the copolymerized product of a mixture of acrylic acid, methacrylic acid, and 2-hydroxyethy methacrylate phosphates of Formula 1, e.g., in a molar ratio of about 85:11:4.

1.13 Any foregoing composition wherein the acidic polymer comprises 0.1 to 10 weight % phosphate/acrylate co-polymer, e.g., 0.2 to 9 weight % phosphate/acrylate co-polymer, e.g., 0.3 to 8 weight % phosphate/acrylate co-polymer, e.g., 0.4 to 7 weight % phosphate/acrylate co-polymer, e.g., 0.5 to 6 phosphate/acrylate co-polymer, e.g., e.g., 0.5 to 5 weight % phosphate/acrylate co-polymer, e.g., 0.5 to 4 weight % phosphate/acrylate co-polymer, e.g., 0.5 to 3 weight % phosphate/acrylate co-polymer, e.g., 0.5 to 2 weight % phosphate/acrylate co-polymer, e.g., 1 to 10 weight % phosphate/acrylate co-polymer, e.g., 1 to 8 weight % phosphate/acrylate co-polymer, e.g., 1 to 6 weight % phosphate/acrylate co-polymer, e.g., 1 to 5 weight % phosphate/acrylate co-polymer, e.g., 1 to 4 weight % phosphate/acrylate co-polymer, e.g., 1 to 3 weight % phosphate/acrylate co-polymer, e.g., 1 to 2 weight % phosphate/acrylate co-polymer.

1.14 Any foregoing composition wherein the acidic polymer is present in a total amount of 0.1-2 weight % based on the total weight of the composition; or 0.5-1.5 weight % based on the total weight of the composition (e.g., about 1.2 weight % based on the total weight of the composition).

1.15 Any foregoing composition wherein the acidic polymer comprises a phosphate/acrylate co-polymer, in an amount of 1 to 12%; e.g., 2-4%.

1.16 Any foregoing composition wherein the nonionic polymer is selected from one or more poly(alkylene oxide) polymers.

1.17 Any foregoing composition wherein the nonionic polymer is selected from polyethylene glycols, polypropylene glycols, poloxamers, co-polymers of polyethylene glycol and polypropylene glycol, and mixtures thereof.

1.18 Any foregoing composition wherein the nonionic polymer has a molecular weight of at least 3000 D, e.g., 6 kD to 250 kD, e.g., 8 kD.

1.19 Any foregoing compositions wherein the nonionic polymer comprises polyethylene glycol of MW 5 kDa-35 kDa, in an amount of 3% to 8% by weight; e.g. 4% to 6% by weight; e.g., 4%; e.g., 5%.

1.20 Any foregoing compositions wherein the nonionic polymer is 3-6% polyethylene glycol having a molecular weight of 5 kDa to 10 kDa, e.g. 8 kDa.

1.21 Any foregoing composition wherein the polyamine compound comprises lysine, in free or salt form.

1.22 Any foregoing composition wherein the polyamine compound comprises lysine hydrochloride salt.

1.23 Any foregoing composition wherein the stabilizing amount of polyamine compound, is an amount sufficient to substantially interfere with interaction between the at least one polyphosphate and/or an optional a cationic active agent and the acidic polymer, e.g. an amount sufficient to inhibit formation of a precipitate or reduction of the efficacy of the cationic active agent.

1.24 Any foregoing composition wherein the composition comprises 0.5%-5% lysine, in free or salt form, e.g., 1% lysine, based on the total weight of the composition.

1.25 Any foregoing composition wherein the polyamine is lysine in free or salt form and the composition further comprises glutamic acid, in free or salt form, wherein the combined amount of lysine and glutamic acid is 1 to 10%; e.g., a combination of lysine and glutamic acid in a weight ratio of lysine:glutamic acid of 3:1 to 5:1, wherein the weight % is calculated on the basis of the weight of the free amino acids.

1.26 Any foregoing composition wherein the composition comprises lysine in the form of the hydrochloride salt.

1.27 Any foregoing composition wherein the composition comprises 0.5-5% lysine hydrochloride, e.g. 1% lysine hydrochloride.

1.28 Any foregoing composition further comprising glutamic acid, in free or salt form, 1.29 Any foregoing composition wherein the polyamine, in free or orally acceptable salt form, is lysine, and the composition further comprises glutamic acid, the lysine and the glutamic acid each being in free or orally acceptable salt form, in a total amount of 1 to 10%.

1.30 Any foregoing composition wherein the polyamine, in free or orally acceptable salt form is lysine, and the composition further comprises glutamic acid, each of the lysine and the glutamic acid being in free or orally acceptable salt form and in a weight ratio of lysine: glutamic acid of 3:1 to 5:1, weight being calculated on the basis of the free amino acid.

1.31 Any foregoing composition wherein the cationic active agent is an antimicrobial agent and is present in an antimicrobially effective concentration.

1.32 Any foregoing composition wherein the cationic active agent is selected from one or more of quaternary ammonium surfactants (such as cetyl pyridinium chloride (CPC), benzalkonium chloride, cetyl trimethylammonium bromide or chloride, didecyldimethylammonium chloride, benzethonium chloride), bisguanides (such as chlorhexidine digluconate), cationic amino acids (such as arginine), metal cations (such as zinc, calcium, or stannous ions), or combinations thereof, e.g. 1.32.1. Any foregoing composition wherein the composition is an oral care product, e.g., a mouthwash, and comprises an effective amount of an orally acceptable antimicrobial cationic active agent selected from one or more of quaternary ammonium surfactants (such as cetyl pyridinium chloride (CPC)), bisguanides (such as chlorhexidine digluconate), cationic amino acids (such as arginine), metal cations (such as zinc, calcium, or stannous ions), and combinations thereof; or 1.33 Any foregoing composition wherein the cationic active agent comprises a pyridinium surfactant, e.g., cetyl pyridinium chloride (CPC).

1.34 Any foregoing composition wherein the cationic active agent comprises chlorhexidine.

1.35 Any foregoing composition wherein the cationic active agent comprises arginine.

1.36 Any foregoing composition wherein the cationic active agent comprises zinc ions.

1.37 Any foregoing composition wherein the cationic active agent is provided by an orally acceptable salt selected from zinc salts, stannous salts, pyridinium salts, and bisguanide salts.

1.38 Any foregoing composition wherein the cationic active agent is provided by a salt selected from cetyl pyridinium chloride and chlorhexidine digluconate.

1.39 Any foregoing composition wherein the cationic active agent is provided by a zinc salt, stannous salt or combination thereof.

1.40 Any foregoing composition wherein the effective amount of cationic active agent, in free or salt form, is present and comprises cetyl pyridinium chloride, in an amount of 0.05 to 0.1%, e.g., about 0.075%.

1.41 Any foregoing composition wherein the effective amount of cationic active agent, in free or salt form, is present and comprises chlorhexidine digluconate, in an amount of 0.1 to 0.2%, e.g., about 0.12%.

1.42 Any foregoing composition comprising an antimicrobial phenolic compound, e.g., selected from *magnolia* extract compounds (e.g. magnolol or honokiol), phenol, cresols (e.g., thymol), halogenated (e.g., chlorinated or brominated) phenols (e.g. hexachlorophene, trichlorophenol, tribromophenol, or pentachlorophenol); or an antimicrobial halogenated di-phenyl compound, e.g., triclosan, or triclocarban.

1.43 Any foregoing composition wherein the composition comprises taurine, e.g., 0.3-3% taurine.

1.44 Any foregoing composition wherein the composition comprises greater than 40% water; e.g., greater than 50% water.

1.45 Any foregoing composition wherein the composition comprises 58% to 70% water; e.g., 60% to 68% water.

1.46 Any foregoing composition wherein the composition comprises one or more of a thickener, a buffer, a humectant, a surfactant, an abrasive, a sweetener, a flavorant, a pigment, a dye, an anti-caries agent, an anti-bacterial agent, a whitening agent, a desensitizing agent, a preservative, or a mixture thereof.

1.47 Any foregoing composition wherein the composition contains a bluing agent, e.g., a blue dye or blue pigment, e.g., capable of imparting color to the composition and/or providing a whiter appearance to a yellow surface, for example the surface of a tooth.

1.48 Any foregoing composition wherein the composition comprises a buffer wherein the buffer comprises sodium hydroxide.

1.49 Any foregoing composition wherein the composition comprises a humectant.

1.50 Any foregoing composition wherein the composition comprises a humectant, wherein the humectant is a mixture of glycerin, sorbitol, and propylene glycol.

1.51 Any foregoing composition wherein the composition comprises an anionic surfactant.

1.52 Any foregoing composition wherein the composition comprises an abrasive.

1.53 Any foregoing composition wherein the composition comprises an abrasive, wherein the abrasive comprises silica.

1.54 Any foregoing composition wherein the composition comprises a sweetener.

1.55 Any foregoing composition wherein the composition comprises a sweetener, wherein the sweetener is sodium saccharin.

1.56 Any foregoing composition wherein the composition comprises a flavorant.

1.57 Any foregoing composition wherein the composition comprises a dye.

1.58 Any foregoing composition wherein the composition comprises an anti-caries agent.

1.59 Any foregoing composition wherein the composition comprises a fluoride ion source.

1.60 Any foregoing composition wherein the composition comprises a fluoride ion source, wherein the fluoride ion source is stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, or a mixture thereof.

1.61 Any foregoing composition wherein the composition comprises a whitening agent.

1.62 Any foregoing composition wherein the composition comprises a whitening agent, wherein the whitening agent is hydrogen peroxide.
1.63 Any foregoing composition wherein the composition comprises a desensitizing agent, a vitamin, a preservative, an enzyme, or a mixture thereof.
1.64 Any foregoing composition wherein each of the anionic polymer, the nonionic polymer, the polyamine, and the cationic active agent (if any) are each orally acceptable, e.g., safe for administration to the oral cavity of a human at relevant concentrations.
1.65 Any foregoing composition wherein the composition is a mouthwash, toothpaste, tooth gel, tooth powder, non-abrasive gel, foam, mouth spray, lozenge, oral tablet, dental implement, or pet oral care product.
1.66 Any foregoing composition wherein the composition is a mouthwash, e.g., wherein all ingredients of the composition are orally acceptable, e.g., safe and palatable for administration to the oral cavity of a human at relevant concentrations.
1.67 Any foregoing composition having a pH between the isoelectric point of the acidic polymer and the isoelectric point of the polyamine compound.
1.68 Any foregoing composition having a pH of 3.5 to 8.5 (i.e., 4.0-5.0 or 6.0-6.5, e.g., 4.0-5.0, 4.3-4.9, or 4.6).
1.69 Any foregoing composition wherein the composition comprises an anionic surfactant, wherein the anionic surfactant is selected from sodium laureth sulfate and sodium lauryl sulfate.
1.70 Any foregoing composition further comprising sodium lauryl sulfate in an amount of up to 1%.
1.71 Any foregoing composition further comprising sodium lauryl sulfate, e.g., 0.1-1.5%.
1.72 Any foregoing composition which is a mouthwash comprising 0.1-2%, e.g., about 1.2% phosphate/acrylate co-polymer having a molecular weight of 20 to 30 kDa; 0.05-0.1%, e.g., about 0.075% cetyl pyridinium chloride; 0.5-5%, e.g., 1-2%, total polyphosphates (i.e., sodium tripolyphosphate or a combination of sodium tripolyphosphate and sodium acid pyrophosphate); 0.5-5%, e.g., about 1% lysine; 0.1-2%, e.g., about 1% polyethylene glycol having molecular weight of 6-10 kDa, e.g. about 8 kDa, and 58-70% water.
1.73 Any foregoing composition wherein the composition has any one or more or all of the following features:
a) the acidic polymer comprises a combination of a phosphate/acrylate co-polymer in a total amount of 0.1-2%; e.g., about 1.2%;
b) the nonionic polymer comprises a combination of (i) polyethylene glycol having an average molecular weight of 5 kDa to 35 kDa, e.g., PEG 8 k or PEG 35 k, and (ii) poloxamer 407, in a total amount of 0.1-2%; e.g., 1% polyethylene glycol and 0.5-1.5%, e.g., about 1%, poloxamer;
c) the polyphosphate comprises sodium tripolyphosphate in an amount of 0.1-5%, e.g. 1-2%; or a combination of sodium tripolyphosphate and sodium acid pyrophosphate each present in an amount of about 0.1-1% (e.g., 0.5%);
d) the polyamine, in free or salt form, is lysine in an amount of 0.5-5%, e.g. 1%;
e) the water is present in an amount of 58-70%; and
f) the cationic active agent is present in an effective amount, in free or orally acceptable salt form and comprises cetyl pyridinium chloride, in an amount of 0.05 to 0.1%, e.g., about 0.075%, wherein the composition is a mouthwash, further comprising humectant, e.g., propylene glycol, glycerin and sorbitol in an amount of 20-40%, and about 1%, flavoring, sweetener, preservative (e.g. sodium benzoate or potassium sorbate in an amount of 0.04%-0.06%), and dye (e.g., Blue Dye #1)
wherein all ingredients are orally acceptable, e.g., safe and palatable at relevant concentrations for use in a mouthwash;
wherein all amounts are by weight of the total composition.
1.74 Any foregoing composition, other than as specifically designated as an oral care composition.
1.75 Any foregoing composition, wherein the composition provides enhanced anti-bacterial effects on the surface of a tooth for an extended period of time following use.
1.76 Any foregoing composition, wherein the composition provides enhanced anti-bacterial effects on the surface of a tooth for a period of 18 hours following use.

Further claimed is the use of a polyamine, e.g., lysine, in free or orally acceptable salt form, to stabilize interactions between one or more anti-attachment agents (i.e., a polyphosphate and/or acidic polymer) and a cationic active agent such as cetyl pyridinium chloride, e.g., according to any of Composition 1, et seq., e.g. comprising an acidic polymer, a nonionic polymer, and an effective amount of a cationic active agent, in free or orally acceptable salt form; for example, use in any of the foregoing Compositions 1, et seq.

As used herein, an "oral care composition" refers to a composition for which the intended use can include oral care, oral hygiene, or oral appearance, or for which the intended method of use can comprise administration to the oral cavity. The term "oral care composition" thus specifically excludes compositions which are highly toxic, unpalatable, or otherwise unsuitable for administration to the oral cavity. In some embodiments, an oral care composition is not intentionally swallowed, but is rather retained in the oral cavity for a time sufficient to affect the intended utility. The oral care compositions as disclosed herein may be used in nonhuman mammals such as companion animals (e.g., dogs and cats), as well as by humans. In some embodiments, the oral care compositions as disclosed herein are used by humans. Oral care compositions include, for example, dentifrice and mouthwash. In some embodiments, the disclosure provides mouthwash formulations.

As used herein, "orally acceptable" refers to a material that is safe and palatable at the relevant concentrations for use in an oral care formulation, such as a mouthwash or dentifrice.

As used herein, "orally acceptable carrier" refers to any vehicle useful in formulating the oral care compositions disclosed herein. The orally acceptable carrier is not harmful to a mammal in amounts disclosed herein when retained in the mouth, without swallowing, for a period sufficient to permit effective contact with a dental surface as required herein. In general, the orally acceptable carrier is not harmful even if unintentionally swallowed. Suitable orally acceptable carriers include, for example, one or more of the following: water, a thickener, a buffer, a humectant, a surfactant, an abrasive, a sweetener, a flavorant, a pigment, a dye, an anti-caries agent, an anti-bacterial, a whitening agent, a desensitizing agent, a vitamin, a preservative, an enzyme, and mixtures thereof.

As used herein, "cationic active agent" means an agent which is cationic in aqueous solution at neutral pH and which provides some benefit, e.g. antimicrobial activity. In an oral care formulation, the cationic active agent may provide anti-gingivitis, anticavity and/or antierosion activity to the teeth, gums, or oral cavity. While in aqueous formulation, the agent will generally be in solution, but it may be introduced to the formulation formulated in free or salt form. In certain embodiments, for example in certain oral care formulations, the cationic active agent may be selected from one or more of quaternary ammonium surfactants (such as cetyl pyridinium chloride (CPC)), bisguanides (such as chlorhexidine digluconate), cationic amino acids (such as arginine), metal cations (such as zinc, calcium, or stannous ions), or combinations thereof.

As used herein, "acidic polymer" means a polymer comprising monomers bearing acidic groups, for example carboxy and/or phosphate groups, for example selected from one or more of synthetic anionic linear or branched polycarboxylates and phosphate/acrylate co-polymers and mixtures thereof, which are present in an amount to facilitate attachment to a tooth. The acidic polymer should have a relatively low isoelectric point, e.g., pH 5 or less. The appropriate molecular weight will vary depending on the specific polymer, the degree of crosslinking or branching, and the proportion of acidic functional groups, but in general, the molecular weight is greater than 5000 g/mol. In various embodiments, the acidic polymer could be in a linear or nonlinear (i.e. branched) form or a mixture of linear and branched forms, the backbone or side chains could contain various hydrophobic moieties such as methyl methacrylate monomers, alkane chains, etc., and/or as hydrophilic uncharged moieties such as PEG or PPG, as well as moieties bearing acidic functional groups. Examples of acidic polymers include synthetic anionic linear polycarboxylates, phosphate/acrylate co-polymers, and combinations thereof. The acidic polymer can be made up of copolymers or homopolymers of acidic functional monomers or mixtures thereof.

As used herein, a "nonionic polymer" is a water soluble polymer which does not form an ionic species at relevant pH, e.g., between pH 3 and 10, for example in certain embodiments selected from one or more poly(alkylene oxide) polymers, e.g., selected from polyethylene glycols (PEG), polypropylene glycols (PPG), poloxamers (block co-polymers of PEG and PPG), random copolymers of PEG and PPG, and mixtures thereof. In some embodiments, the nonionic polymer has a molecular weight of at least 3000 D, e.g., 6 kDa to 250 kDa. The molecular weight may vary depending on the particular type of polymer, the degree of branching, if any, and the concentration used. In particular embodiments, the nonionic polymer comprises a mixture of (i) polyethylene glycol (MW 5 kDa-35 kDa) and (ii) poloxamer (i.e., an ethylene oxide/propylene oxide block copolymer), e.g., poloxamer 407, which is a triblock copolymer consisting of a central hydrophobic block of polypropylene glycol flanked by two hydrophilic blocks of polyethylene glycol, wherein the approximate length of the two PEG blocks is about 101 repeat units while the approximate length of the propylene glycol block is about 56 repeat units, available commercially for example as Pluronic F127 (BASF).

As used herein "polyamine compound" means a molecule having at least two primary or secondary amine groups, for example having an isoelectric point of greater than pH 8.5, for example pH 9-10. Examples of polyamines include ethylene diamine, lysine, or histadine, as well as polymers such as Lupasol P, which is a polyethylenimine. The polyamine must be safe for its intended use. Where the composition is an oral care composition, the polyamine must be orally acceptable. The polyamine may be provided in free or acid addition salt form. In certain embodiments the polyamine compound is lysine.

As used herein "polyphosphate" refers to one or more compounds having a chain of two or more phosphate anions, which are present in an amount to facilitate attachment to the surface of a tooth. Examples of suitable polyphosphates are alkali pyrophosphates or alkali polyphosphates. For example, the polyphosphates according to this disclosure may be sodium tripolyphosphate, tetrasodium pyrophosphate, sodium acid pyrophosphate, tetrapotassium pyrophosphate, sodium hexametaphosphate or combinations thereof. In various embodiments, the polyphosphate used comprises a mixture of sodium tripolyphosphate and sodium acid pyrophosphate. The sodium tripolyphosphate and sodium acid pyrophosphate may be present in a ratio of 2:1 to 1:2. In some embodiments, the sodium acid pyrophosphate may also be used to adjust the pH of the composition.

As used herein, "phosphate/acrylate co-polymer" refers to a polymer made up of acrylate monomers and phosphate-bearing monomers, e.g., a co-polymerized product of a mixture of acrylic acid, methacrylic acid, and a mixture of compounds of Formula 1:

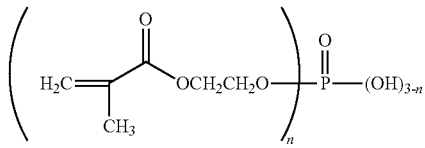

wherein n is 0, n is 1 and n is 2. In some embodiments, the phosphate/acrylate co-polymer is a co-polymerized product of a mixture of acrylic acid, methacrylic acid, and 2-hydroxyethyl methacrylate phosphates of Formula 1, comprising acrylic acid in a molar percentage of 80-90%, e.g., about 85%; methacrylic acid in a molar percentage of 5-15%, e.g., about 11%, and hydroxyethyl methacrylate phosphates of Formula 1 in a molar percentage of 2-6%, e.g., about 4%. In some embodiments, the phosphate/acrylate co-polymer has an average molecular weight of from 10 to 40 kDa, e.g., 20 to 30 kDa. Phosphate/acrylate co-polymers as described include commercially available polymers, e.g. DV8801 (Rhodia), sometimes referred to herein as DV. The phosphate side group of a phosphate/acrylate co-polymer, as disclosed herein, may function as an anchor to deposit the co-polymer onto the tooth surface thereby forming a physical layer on the tooth surface that may inhibit staining and/or biofilm formation. For example, in a particular embodiment (the embodiment used in the Examples below), the phosphate/acrylate copolymer is a random copolymer having a weight average molecular weight of about 20,000 to 30,000 grams per mole that is the copolymerized product of a mixture of, in the relative amounts set forth in Table 1 below, 2-hydroxyethy methacrylate phosphates, acrylic acid, and methacrylic acid.

TABLE 1

| Monomer Name and Structure | Monomer Weight Ratio (weight %) | Monomer Molar Ratio (Mole %) |
| --- | --- | --- |
| 2-hydroxyethyl methacylate phosphates 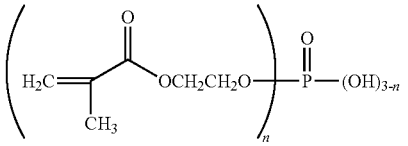 mixture of n = 0, n = 1, and n = 2 | 11 | 4 |
| 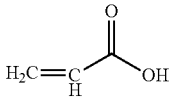 acrylic acid | 75 | 85 |
| 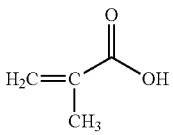 methacrylic acid | 14 | 11 |

As used herein, "synthetic anionic linear polycarboxylate" refers to a polymer synthesized by using an olefinically or ethylenically unsaturated carboxylic acid that contains an activated carbon-to-carbon olefinic double bond and at least one carboxyl group. The acid contains an olefinic double bond that readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrilacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other olefinic monomers copolymerizable with such carboxylic monomers include vinyl acetate, vinyl chloride, dimethyl maleate and the like. The synthetic anionic linear polycarboxylate is mainly a hydrocarbon with optional halogen and O-containing substituents and linkages as present in for example ester, ether, and OH groups. The copolymers preferably contain sufficient carboxylic salt groups for water-solubility. The terms "synthetic" and "linear" do not include known thickening or gelling agents comprising carboxymethylcellulose and other derivatives of cellulose and natural gums, nor Carbopols having reduced solubility due to cross-linkages.

As used herein, a "tartar control agent" refers to a compound or a mixture of compounds that inhibit the formation of tartar, a mixture of calcium phosphates on organic matrices, and/or the deposition of plaque on teeth to form tartar (calculus).

As used herein, "chemical stain" refers to a discoloration of a surface, e.g., a dental surface caused by adsorption or absorption of a colored agent on or into the surface, or caused by chemical reaction of material of the surface (e.g., dental enamel) with a colored or noncolored agent contacting the surface. "Chemical staining" herein means formation and/or development of a chemical stain.

As used herein, "dental surface" refers to a surface of a natural tooth or a hard surface of artificial dentition including a crown, cap, filling, bridge, dental implant and the like. In some embodiments, the dental surface is a natural tooth.

Oral Care Compositions:

In some embodiments the compositions are oral care compositions, in accordance with Composition 1, et seq. for example mouthwashes. Any of the compositions of Composition 1, et seq. is suitable for oral care use, provided the ingredients are orally acceptable. In some embodiments, the mouthwash of Composition 1 comprises an effective amount of an orally acceptable cationic active agent, which is an antimicrobial, antigingivitis, anti-erosion and/or anti-caries agent, e.g. a cationic active agent selected from one or more of quaternary ammonium surfactants (such as cetyl pyridinium chloride (CPC)), bisguanides (such as chlorhexidine digluconate), cationic amino acids (such as arginine), metal cations (such as zinc, calcium, or stannous ions), or combinations thereof. The orally acceptable cationic active agent may be present in an effective amount, for example an antimicrobial, antigingivitis, anti-erosion and/or anti-caries amount. The precise amount will depend on the particular active agent and the condition to be treated or prevented, but in various embodiments, antimicrobially effective levels of CPC in a mouthwash would include amounts from 0.05 to 0.1%, e.g., about 0.075%; antimicrobially effective levels of chlorhexidine digluconate in a mouthwash would include amounts from 0.1-0.2%, e.g., about 0.12%; anti-erosion or antimicrobial levels of metal cations such as zinc (e.g., zinc citrate or other soluble salt) or stannous (e.g., stannous fluoride and/or stannous chloride) would be on the order of 100-1500 ppm.

The oral care composition used in the present disclosure comprise significant levels of water. Water employed in the preparation of commercial oral compositions should be deionized and free of organic impurities. The amount of water in the compositions includes the free water that is added plus that amount which is introduced with other materials.

Mouthwashes frequently contain significant levels of ethanol, which is often needed to solubilize essential oils and to prevent bacterial contamination. High levels of ethanol may be undesirable, because in addition to the potential for abuse by ingestion, the ethanol may exacerbate conditions like xerostoma. Accordingly, in some embodiments, the oral care compositions of the invention are substantially free of ethanol, e.g., contain less than 1% ethanol.

Humectants can enhance the viscosity, mouthfeel, and sweetness of the product, and may also help preserve the product from degradation or microbial contamination. Suitable humectants include edible polyhydric alcohols such as glycerin, sorbitol, xylitol, propylene glycol as well as other polyols and mixtures of these humectants. Sorbitol may in some cases be provided as a hydrogenated starch hydrolysate in syrup form, which comprises primarily sorbitol (the product if the starch were completely hydrolyzed to glucose, then hydrogenated), but due to incomplete hydrolysis and/or presence of saccharides other than glucose, may also include other sugar alcohols such mannitol, maltitol, and longer chain hydrogenated saccharides, and these other sugar alcohols also function as humectants in this case. In some embodiments, humectants are present at levels of 5% to 40%, e.g., 20% to 30% by weight.

Flavorings for use in the present invention may include extracts or oils from flavorful plants such as peppermint, spearmint, cinnamon, wintergreen, and combinations thereof, cooling agents such as menthol, methyl salicylate, and commercially available products such as OptaCool® from Symrise, as well as sweeteners, which may include polyols (which also function as humectants), saccharin, acesulfame, aspartame, neotame, *stevia* and sucralose.

Further provided is a method (Method A) for the treatment and/or inhibition of a chemical stain, plaque, and/or tartar on a dental surface, comprising applying a composition (i.e., Composition 1, et seq.) to the oral cavity or to the surface of a tooth.

Further provided herein is Method A as follows:
A.1 Method A wherein the composition is Composition 1, et seq., e.g., wherein the ingredients are orally acceptable, e.g. wherein the composition is a mouthwash.
A.2 Method A or A.1 wherein the method is for the treatment of a chemical stain, plaque, and/or tartar on the dental surface.
A.3 Method A.2 wherein the method is for the treatment of a chemical stain on the dental surface.
A.4 Method A.2 wherein the method is for the treatment of plaque on the dental surface.
A.5 Method A.2 wherein the method is for the treatment of tartar on the dental surface.
A.6 Method A or A.1 wherein the method is for the inhibition of a chemical stain, plaque, and/or tartar on the dental surface.
A.7 Method A.6 wherein the method is for the inhibition of a chemical stain on the dental surface.
A.8 Method A.6 wherein the method is for the inhibition of plaque on the dental surface.
A.9 Method A.6 wherein the method is for the inhibition of tartar on the dental surface.
A.10 Method A or A.1-A.9 wherein the dental surface is a human tooth.
A.11 Method A or A.1-A.10 wherein the composition is contacted with the dental surface by brushing.

Further provided is a method (Method B) for the treatment and/or inhibition of gum disease comprising applying a composition (i.e., Composition 1, et seq.) to the oral cavity or to the surface of a tooth.

Further provided herein is Method B as follows:
B.1 Method B wherein the composition is Composition 1, et seq., e.g., wherein the ingredients are orally acceptable, e.g. wherein the composition is a mouthwash.
B.2 Method B or B.1 wherein the method is for the treatment of gum disease.
B.3 Method B, B.1, or B.2 wherein the gum disease is gingivitis.
B.4 Method B, B.1, or B wherein the gum disease is periodontitis.
B.5 Method B or B.1 wherein the method is for the inhibition of gum disease.
B.6 Method B, B.1, or B.5 wherein the gum disease is gingivitis.
B.7 Method B, B.1, or B.5 wherein the gum disease is periodontitis.
B.8 Method B or B.1-B.7 wherein the oral cavity is a human oral cavity.
B.9 Method B or B.1-B.8 wherein the composition is contacted with the oral cavity by brushing.

Further provided is a method (Method C) for the treatment and/or inhibition of halitosis comprising applying a composition (i.e., Composition 1, et seq.) to the oral cavity or to the surface of a tooth.

Further provided herein is Method C as follows:
C.1 Method C wherein the composition is Composition 1, et seq., e.g., wherein the ingredients are orally acceptable, e.g. wherein the composition is a mouthwash.
C.2 Method C or C.1 wherein the oral cavity is a human oral cavity.
C.3 Method C, C.1, or C.2 wherein the composition is contacted with the oral cavity by brushing.

Further provided is a method (Method. D) for inhibiting biofilm formation on a dental surface comprising applying a composition (i.e., Composition 1, et seq.) to the oral cavity or to the surface of a tooth.

Further provided herein is Method D as follows:
D.1 Method D wherein the composition is Composition 1, et seq., e.g., wherein the ingredients are orally acceptable, e.g. wherein the composition is a mouthwash.
D.2 Method D or D.1 wherein the dental surface is a human tooth.
D.3 Method D, D.1, or D.2 wherein the composition is contacted with the dental surface by brushing.

Further provided is a method (Method E) for treating and/or inhibiting bacteria from sticking together and growing into bigger colonies in an oral cavity comprising applying a composition (i.e., Composition 1, et seq.) to the oral cavity or to the surface of a tooth.

Further provided herein is Method E as follows:
E.1 Method E wherein the composition is Composition 1, et seq., e.g., wherein the ingredients are orally acceptable, e.g. wherein the composition is a mouthwash.
E.2 Method E or E.1 wherein the oral cavity is a human oral cavity.
E.3 Method E, E.1, or E.2 wherein the composition is contacted with the oral cavity by brushing.

Further provided are Compositions 1, et seq. for use in any of Methods A-E.

As used herein, "inhibition" refers to reduction of stains that would otherwise form or develop subsequent to the time of the treatment. Such inhibition can range from a small but observable or measurable reduction to complete inhibition of subsequent staining, by comparison with an untreated or placebo-treated dental surface.

Where the dental surface is substantially free of chemical stains, Method A, e.g., A.1-A.11, is effective to inhibit formation and development of new chemical stains, as can occur for example by oral use of tobacco products (including smoking) or by drinking tea, coffee, red wine, or coke, subsequent to treatment according to the method. Where the dental surface already possesses some degree of chemical staining, Method A, e.g., A.1-A.11, is effective to inhibit further development of the existing stain. In some embodiments, the Method A, e.g., A.1-A.11, can remove, partially or completely, an existing chemical stain as well as inhibit subsequent staining.

EXAMPLES

Example 1—Formulation

Compositions were formulated having combinations of Rhodia DV8801 (a.k.a. Mirapol 8801) (DV), lysine (Lys), sodium tripolyphosphate (STPP), sodium acid pyrophosphate (SAPP) and polyethylene glycol having a molecular weight of about 8,000 daltons. The formulations are mixed together and result in single phase solutions with a PEG concentrated layer on top, and a DV-Lys concentrated layer on the bottom.

Exemplary formulations were manufactured through the following method. Poloxamer and polyethylene glycol having a molecular weight of about 8,000 daltons were first fully dissolved in water. Once formed, polyphosphates (i.e., STPP and/or SAPP), lysine and Rhodia DV8801 were added. Next, cetyl pyridinium chloride is added, followed by all remaining formulation components. Generally, polyethylene glycol is added last to such formulations; however, it was found that adding the polyethylene glycol last resulted in a large increase in dissolving time, typically overnight.

Using the above method, the following compositions were created.

TABLE 2

Single phase mouthwash formulations

| Material | STPP/SAPP | STPP/SAPP w/o CPC | DV | DV w/o CPC |
|---|---|---|---|---|
| Water | 61.18 | 68.68 | 60.96 | 68.46 |
| Poloxomer | 1 | 1 | 1 | 1 |
| Polyethylene Glycol (8,000D) | 1 | 1 | 1 | 1 |
| Lysine HCl | 1 | 1 | 1 | 1 |
| Sodium Tripolyphosphate (STPP) | 0.5 | 0.5 | — | — |
| Sodium Acid Pyrophosphate (SAPP) | 0.5 | 0.5 | — | — |
| Rhodia DV8801 (in 41% solution) | — | — | 1.22 | 1.22 |
| CPC (in 1% solution) | 7.5 | — | 7.5 | — |
| Preservative | 0.05 | 0.05 | 0.05 | 0.05 |
| Humectants | 27 | 27 | 27 | 27 |
| Flavorants and Colorants | 0.2 | 0.2 | 0.2 | 0.2 |
| Total | 100 | 100 | 100 | 100 |

Example 2—Antibacterial Efficacy of Formulations

Studies were carried out to analyze the antibacterial efficacy of the discussed single phase solutions containing DV, Lysine, STPP, SAPP and PEG. Studies were also conducted using a commercial formulation as a control.

TABLE 3

Commercial Formulation 1

| Material | Commercial Formulation 1 |
|---|---|
| Water | q.s. |
| Pluronic F127 | 0.1-2 |
| PEG 8K | 0.0 |
| Lysine HCl | 0.0 |
| STPP | 0.0 |
| Mirapol 8801 (41%) | 0.0 |
| Cetylpyridinium chloride | 0.01-0.1 |
| Preservative | 0.01-0.1 |
| Humectants | 0-40 |
| Flavor | 0.05-1 |
| Color | 0.0001-0.005 |

The active attachment biofilm model (Extrecate et al., Caries Research 2010; 44:372-379) was used to measure antibacterial efficacy of the mouthwash formulations. In this model, 24-HAP discs were clamped onto a sterile metal lid. The lid was then inoculated in 2% unstimulated saliva in McBain medium for 24 hours at 37° C. on a 24-well plate under anaerobic conditions. After initial attachment, the biofilms were transferred into fresh growth media for maturation.

Treatment was performed after formation of biofilm (i.e., 24 hours). Discs were treated for 10 minutes at room temperature with 1.6 ml mouthwash formulations. The lid was subsequently transferred to a new plate for washing with 1.7 ml 25% Tryptic Soy Buffer (repeated 3 times). The biofilms were then transferred into McBain medium and incubated anaerobically at 37° C. The discs were treated seven times over a 5-day period and the resulting biofilms were harvested using sonication. The harvested biofilms were subjected to ATP metabolic assay (supplied by ThermoFisher Scientific) and plated on 5% sheep blood agar plate to determine total colony counts. Results were reported as log(CFU/ml) for four replicates of each sample.

It is known that polyphosphates or phosphate polymers can form complexes with CPC, which would cause the CPC to lose antibacterial efficacy. For this reason, the efficacy of a series of formulas were measured via SIKT (short interval kill test) and compared with the Commercial Formulation 1 in order to first identify potential ingredient combination candidates. Several formulations were then selected and subjected to further analysis via ACTA and anti-attachment models.

Simple solutions as defined in Table 4 below were exposed to planktonic bacteria for 30 seconds. Figure 1 shows the efficacy of samples ranging in weight % of DV. As observed, no solution tested was significantly comparable to the SIKT efficacy of the Commercial Formulation 1. Only in the case of 0.25% DV use level did bacterial viability drop below 50%.

TABLE 4

SIKT for various simple solutions containing DV

| Formulation Details (wt. %) | Bacterial Viability (%) |
|---|---|
| 0.25% DV, 1% PEG8k, 1% Lys | 55.05 |
| 0.5% DV, 1% PEG8k, 1% Lys | 71.17 |
| 0.75% DV, 1% PEG8k, 1% Lys | 86.48 |
| 1% DV, 1% PEG8k, 1% Lys | 75.02 |
| 0.25% DV, 2% PEG8k, 1% Lys | 44.30 |
| 0.5% DV, 2% PEG8k, 1% Lys | 87.99 |

TABLE 4-continued

SIKT for various simple solutions containing DV

| Formulation Details (wt. %) | Bacterial Viability (%) |
|---|---|
| 0.75% DV, 2% PEG8k, 1% Lys | 93.01 |
| 1% DV, 2% PEG8k, 1% Lys | 82.05 |
| Commercial Formulation 1 | 21.91 |

A second set of simple solutions as defined in Table 5 were also exposed to planktonic bacteria for 30 seconds. In contrast to those formulated in Table 4, all samples formulated with STPP/SAPP performed well in comparison to the Commercial Formulation 1, the results of which are illustrated in Table 5 below. The SAPP is present at least in part to adjust the overall pH of the test solutions.

TABLE 5

SIKT for various simple solutions containing 1:1 STPP/SAPP

| Formulation Details (wt. %) | Bacterial Viability (%) |
|---|---|
| 0.5% STPP/SAPP, 1% PEG8k, 1% Lys | 30.70 |
| 1% STPP/SAPP, 1% PEG8k, 1% Lys | 37.77 |
| 1.5% STPP/SAPP, 1% PEG8k, 1% Lys | 33.64 |
| 2% STPP/SAPP, 1% PEG8k, 1% Lys | 33.20 |
| 0.5% STPP/SAPP, 2% PEG8k, 1% Lys | 29.74 |
| 1% STPP/SAPP, 2% PEG8k, 1% Lys | 31.04 |
| 1.5% STPP/SAPP, 2% PEG8k, 1% Lys | 33.22 |
| 2% STPP/SAPP, 2% PEG8k, 1% Lys | 34.41 |
| Commercial Formulation 1 | 21.91 |

The ACTA model represents a more rigorous test for efficacy against bacteria. Several samples were put into full formulations and their cumulative effects on bacteria over a 4-day period were measured, the results of which are shown in Table 6. Versus an untreated sample, both STPP/SAPP and DV-based samples showed 100% efficacy, which was similar (within error) to the Commercial Formulation 1. Further, in order to demonstrate the effectiveness of CPC within these formulations, the ACTA model study was repeated with samples without CPC. Materials like DV and STPP/SAPP act as barriers to bacteria adhesion (anti-attachment) and can therefore give the illusion of antibacterial effect when in fact none exist. A decrease in bacterial viability or ATP output could simply mean that bacteria were repelled from the surface. By comparing identical samples with and without 0.075% CPC, we can better understand the role anti-attachment materials and CPC play within the efficacy profile.

TABLE 6

Percent reduction of bacteria compared to untreated sample under ACTA model

| Formulation Details (wt. %) | Bacterial Reduction (%) |
|---|---|
| 1% STPP/SAPP, 0.075% CPC, 1% Lys | 100 |
| 1% DV, 0.075% CPC, 1% Lys | 100 |
| Commercial Formulation 1 | 83.6 |

Table 7 below shows the difference in efficacy between samples containing zero or 0.075% CPC, comparing with Commercial Formulation 1. As illustrated below, formulations based on STPP/SAPP showed only minor efficacy boosts when the CPC was added. However, those formulated with DV showed almost 4 times better efficacy against bacteria when CPC was included. These differences, however minor or large, do show that CPC is active to bacteria kill in both formulations.

TABLE 7

Percent reduction of bacteria compared to untreated sample under ACTA model

| Formulation Details (wt. %) | Bacterial Reduction (%) |
|---|---|
| 1% STPP/SAPP, 1% Lys (no CPC) | 65.02 |
| 1% STPP/SAPP, 0.075% CPC, 1% Lys | 85.46 |
| 1% DV, 1% Lys (no CPC) | 23.37 |
| 1% DV, 0.075% CPC, 1% Lys | 77.96 |
| Commercial Formulation | 97.11 |

Example 3—Anti-Attachment Evaluation

Studies were also carried out to analyze the combined effects of the formulation on early bacterial attachment, which leads to surface staining. HAP-coated pegs were exposed to the various MW formulations listed overnight in order to reach their equilibrium state. After this time, the pegs were rinsed and then immediately exposed to a bacteria solution containing *A. viscosus* and *S. oralis*, which are known to be early surface colonizers, for 3 hours. Table 8 summarizes the results of this experiment. All samples were screened against the Commercial Formulation 1 discussed above and a whitening commercial formulation (Commercial Formulation 2). In each case, at least a 94% reduction was observed regardless of formulation. Within this range, differences are likely negligible.

TABLE 8

Anti-attachment assay of various stain-prevention formulations

| Formulation Details (wt. %) | Bacterial Reduction (%) |
|---|---|
| 1% STPP/SAPP, 1% Lys | 98.7 |
| 1% DV (no Lys) | 98.0 |
| 1% DV, 0.075% CPC, 1% Lys | 98.2 |
| Commercial Formulation 1 | 94.7 |
| Commercial Formulation 2 | 96.9 |

The data collected shows that samples containing both CPC and stain-prevention materials STPP/SAPP or DV do not show a decrease in efficacy toward bacteria kill. While some of the SIKT measurements seem to indicate a decrease in efficacy, this may be due to the short exposure time of the experiment or decreased active mobility through complexation (DV+CPC). Longer or repeated exposure (i.e., ACTA, anti-attachment), which more closely mimics real-world conditions, consistently show comparable efficacy to that of the Commercial Formulation.

Example 4—Anti-Staining Evaluation

To mitigate staining caused by CPC, comparative evaluations were carried out with Commercial Formulations (i.e., Commercial Formulation 1 and Commercial Formulation 2), which are known to prevent significant staining on oral-relevant surfaces, and formulations containing DV and/or STPP/SAPP.

Saliva-coated HAP discs were exposed to various MW formulations followed by a coffee/tea/wine staining mixture in order to assess their ability to repel stains. Table 8 shows the stain prevention results following a coffee/tea/wine stain. HAP discs exposed to a staining solution do pick up staining, which can be seen in the untreated sample. Following a treatment with Commercial Formulation 1 and Commercial Formulation 2, the discs were shown to have significantly more staining due to deposition of CPC to HAP followed by attraction of anionic stains. The subsequent samples DV, STPP/SAPP, and DV without Lys all exhibit decreased staining from a coffee/tea/wine staining solution. This decreased staining is attributed to the inclusion of anti-stain materials DV and STPP/SAPP, both of which have been shown to inhibit staining to an HAP surface, and on average, shows a significant decrease in deposited stains.

TABLE 9

Stain prevention effect of various mouthwash formulations

| Formulation Details (wt. %) | Color (W) |
| --- | --- |
| 1% STPP/SAPP, 1% Lys | 23.52 |
| 1% DV (no Lys) | 25.34 |
| 1% DV, 0.075% CPC, 1% Lys | 24.57 |
| Commercial Formulation | 38.26 |
| Commercial Formulation 2 containing 0.07% CPC | 43.73 |
| Untreated | 30.03 |

Example 5—Effect of Lysine on the Composition

Compositions were created to test the stabilizing effect that lysine had on the CPC and DV polymer. Mouthwashes were created according to the method of Example 1. Each sample was created with CPC and either STPP or DV. The compositions also contained varied amounts of lysine. The samples created are summarized below.

TABLE 10

Stabilizing effect of lysine on CPC-STPP interaction

| Formulation Details (wt. %) | Bacterial Viability (%) |
| --- | --- |
| 1% STPP, 0.075 CPC (no Lys) | 9 |
| 1% STPP, 0.075 CPC, 1% Lys | 9 |
| 1% STPP, 0.1 CPC, 1% Lys | 9 |
| 1% STPP, 0.1 CPC, 2% Lys | 9 |
| Commercial formulation | 12 |
| Ethanol | 23 |
| PBS | 100 |

As shown above, there was no difference observed in the antibacterial efficacy of the test compositions, regardless of the presence of lysine. However, the results observed from the compositions containing DV showed a significant difference, as shown below.

TABLE 11

Stabilizing effect of lysine on CPC-DV interaction

| Formulation Details (wt. %) | Bacterial Viability at pH 4.6 (%) | Bacterial Viability at pH 6.0 (%) |
| --- | --- | --- |
| 1% DV, 0.075 CPC (no Lys) | 51 | 21 |
| 1% DV, 0.075 CPC, 1% Lys | 47 | 20 |
| 1% DV, 0.075 CPC, 3% Lys | 42 | 21 |
| 1% DV, 0.075 CPC, 5% Lys | 27 | 20 |
| 1% DV, 0.1 CPC, 1% Lys | 63 | 21 |
| 1% DV, 0.1 CPC, 3% Lys | 45 | 19 |
| 1% DV, 0.1 CPC, 5% Lys | 32 | 18 |

TABLE 11-continued

Stabilizing effect of lysine on CPC-DV interaction

| Formulation Details (wt. %) | Bacterial Viability at pH 4.6 (%) | Bacterial Viability at pH 6.0 (%) |
| --- | --- | --- |
| Commercial formulation | 10 | 20 |
| Ethanol | 11 | 19 |
| PBS | 100 | 100 |

As shown in Table 11 above, the formulations at pH 4.6, which is a common pH for oral care compositions, showed that the lysine, when present actively stabilized the compositions by preventing the DV and CPC from interacting with one another. At pH 4.6 however, the results showed that antibacterial efficacy was directly related to the level of Lys present in the formulation—that is, the more Lys in the formulation, the more efficacious CPC was. This trend was observed in formulations containing 0.075% CPC or 0.1% CPC. On the other hand, all compositions tested at pH 6.0, regardless of whether Lys was present, performed equally well and were comparable to Ethanol and Total MW positive controls. These results show that the interactions between DV and CPC are partially dependent on pH.

Example 6—Analysis of Composition for Extended Anti-Bacterial Protection

Additional studies were carried out to test the duration of the anti-bacterial protection provided by the compositions of the present disclosure. The tested composition was observed to be better than a market mouth rinse by a significant margin 18 hours after initial treatment.

Composition A containing 1% STPP and 1% Lysine was prepared similarly to the compositions described above. Composition A is summarized below in Table 12. Commercial Formulation 1 as described above was used as a control.

TABLE 12

| Material | Formula A (wt. %) |
| --- | --- |
| Water | q.s. |
| Poloxomer 407 | 0.4 |
| Lysine HCl | 1 |
| STPP | 1 |
| Cetyl Pyridinium Chloride | 0.075 |
| Sodium Saccharin | 0.02 |
| Sodium Benzoate | 0.05 |
| Glycerin | 7.5 |
| Sorbitol | 5.5 |
| Propylene Glycol | 7 |
| Flavorants and Colorants | 0.17 |
| Total | 100 |

The active attachment biofilm model (Extrecate et al., Caries Research 2010; 44:372-379) was used to measure antibacterial efficacy of mouthwash formulations. In this model, 24-HAP discs were clamped onto a sterile metal lid. The lid was then inoculated in clarified human saliva for 1 hour to form a pellicle. After this time, the discs were treated with salivary bacteria for 6 hours. The discs were removed and then treated with various mouthwash formulations for 1 minute, after which the discs were rinsed three times with buffer solution. The discs were placed back into clarified saliva for 5 minutes, and then treated with salivary bacteria for 18 hours.

After this time, the disks were subjected to two rounds of sonication (2 min by 30 seconds interval) in a volume of 750 µL of dilute tryptic soy broth. The discs were flipped over between sonication treatments in order to ensure full exposure of the disc surface area. Once sonication was completed, the tryptic soy broth solutions were re-suspended and transferred into a new tube containing 1.25 mL of dilute tryptic soy broth to yield a final volume of 2 mL of harvested biofilm. The biofilms were subjected to ATP metabolic assay (Life Technology) and plated on 5% sheep blood agar plate to determine total colony counts. Results were reported as log (CFU/mL) for six replicates of each sample.

Following the procedure outlined above, Formula A consistently produced greater anti-bacterial efficacy than the tested commercial formulation. Specifically, the composition of Formula A showed a 65% reduction in bacterial viability after a period of 18 hours versus an untreated control. On the other hand, Commercial Formulation 1 containing CPC without STPP showed only a 44% reduction in bacterial viability after 18 hours.

It is believed that these results can be attributed to a combination of mechanisms. First, the CPC provides antibacterial efficacy, killing the bacteria present. In addition, the STPP deposits to the surface of the HAP discs and provides anti-attachment efficacy, which creates a surface that limits or prevents further bacteria from depositing/sticking to the surface. This results in an increased protection against bacteria over a greater period of time. Finally, the lysine present in the formulation maintains stability between CPC and STPP, so that the compounds do not deactivate one another.

The assay described above was designed to simulate a single usage during the morning to determine how much bacteria may be remaining at the end of the day. The treatment of salivary bacteria for 18 hours simulates constant salivary interaction with the enamel.

This data demonstrates that "incompatible" ingredients CPC and STPP can be used together in the presence of lysine for greater antibacterial efficacy than CPC alone.

Unless otherwise specified, all percentages and amounts expressed herein and elsewhere in the specification should be understood to refer to percentages by weight. The amounts given are based on the active weight of the material.

While the present invention has been described with reference to embodiments, it will be understood by those skilled in the art that various modifications and variations may be made therein without departing from the scope of the present invention as defined by the appended claims.

The invention claimed is:

1. A single phase composition comprising an aqueous solution comprising
   an anti-attachment agent;
   a nonionic polymer, wherein the nonionic polymer comprises a polyethylene glycol having a molecular weight of 8 kDa;
   a cationic active agent, wherein the cationic active agent is cetyl pyridinium chloride;
   lysine in free or salt form present in an amount of 0.5-5% by weight, based on the total weight of the composition; and
   water,
   wherein the anti-attachment agent comprises one or both of an acidic polymer and at least one polyphosphate, wherein the acidic polymer is a co-polymerized product of a mixture of acrylic acid, methacrylic acid, and a mixture of compounds of Formula 1:

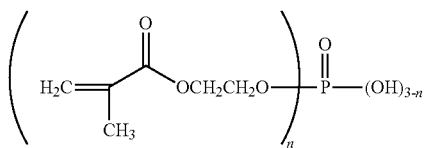

wherein n is 0, n is 1 and n is 2,
   wherein the acidic polymer is present in an amount of 0.1-2% by weight, based on the total weight of the composition,
   wherein the polyphosphate comprises tripolyphosphate in an amount of 1-5% by weight, or a combination of sodium tripolyphosphate and sodium acid pyrophosphate each present in an amount of about 0.1-2.5% by weight, based on the total weight of the composition, and
   wherein the composition has a pH between about 4.0-5.0.

2. The composition of claim 1, wherein the sodium tripolyphosphate and the sodium acid pyrophosphate are present in a ratio between 2:1 and 1:2.

3. The composition of claim 2, wherein the sodium tripolyphosphate and the sodium acid pyrophosphate are present in a ratio of 1:1.

4. The composition of claim 1, wherein the acidic polymer is selected from one or more of synthetic anionic linear or branched polycarboxylates, phosphate/acrylate co-polymers, linear or branched sulfates and combinations thereof.

5. The composition of claim 1, wherein the composition comprises 58% to 70% water.

6. The composition of claim 1 wherein the composition is an oral care composition, wherein the ingredients are orally acceptable, and wherein the composition comprises one or more of a thickener, a buffer, a humectant, a surfactant, an abrasive, a sweetener, a flavorant, a pigment, a dye, an anti-caries agent, an anti-bacterial agent, a whitening agent, a desensitizing agent, a preservative, or a mixture thereof.

7. The composition of claim 1 wherein the composition is a mouthwash.

8. The composition of claim 1, wherein the composition is for removing or preventing surface stains on teeth.

9. The composition of claim 1, wherein the composition is for preventing the attachment of biofilm to the surface of teeth.

10. The composition of claim 1 wherein:
   a) the acidic polymer comprises a combination of a phosphate/acrylate co-polymer in a total amount of 0.1-2% by weight
   b) the nonionic polymer comprises a combination of (i) polyethylene glycol having an average molecular weight of 8 kDa, and (ii) poloxamer 407, in a total amount of 0.1-2% polyethylene glycol and 0.5-1.5% poloxamer;
   c) the polyphosphate comprises sodium tripolyphosphate in an amount of 1-5%; or a combination of sodium tripolyphosphate and sodium acid pyrophosphate each present in an amount of about 0.1-2.5%;
   d) the lysine is in an amount of about 0.5-1.5%;
   e) the water is present in an amount of 58-70%; and
   f) the cationic active agent is present in an effective amount, in free or orally acceptable salt form and comprises cetyl pyridinium chloride, in an amount of 0.05 to 0.1%, wherein the composition is a mouthwash, further comprising humectant, and about 1% flavoring, sweetener, preservative, and dye;

wherein all ingredients are orally acceptable; and wherein all amounts are by weight of the total composition.

* * * * *

UNITED STATES PATENT AND TRADEMARK OFFICE
CERTIFICATE OF CORRECTION

PATENT NO. : 11,497,694 B2
APPLICATION NO. : 16/215028
DATED : November 15, 2022
INVENTOR(S) : Carl Myers et al.

It is certified that error appears in the above-identified patent and that said Letters Patent is hereby corrected as shown below:

In the Specification

In Column 18, Line 50, delete "Figure 1" and insert -- Table 4 --, therefor.

Signed and Sealed this
Eighteenth Day of April, 2023

Katherine Kelly Vidal
*Director of the United States Patent and Trademark Office*